United States Patent [19]

Davis et al.

[11] 3,994,912

[45] Nov. 30, 1976

[54] 1-OXIDES OF SCHIFF BASES OF 6-AMINOPENICILLANIC ACID

[75] Inventors: Douglas Barry Davis, New Hope, Pa.; Ekkehard Böhme, Hightstown; Joseph Edward Dolfini, Princeton, both of N.J.

[73] Assignee: E. R. Squibb & Sons, Inc., Princeton, N.J.

[22] Filed: Mar. 25, 1974

[21] Appl. No.: 454,531

Related U.S. Application Data

[60] Division of Ser. No. 160,935, July 8, 1971, Pat. No. 3,862,181, which is a continuation-in-part of Ser. No. 84,946, Oct. 28, 1970, abandoned.

[52] U.S. Cl. ................... 260/306.7 C; 260/239.1
[51] Int. Cl.² ........................... C07D 499/02
[58] Field of Search ................ 260/239.1, 306.7

[56] References Cited
UNITED STATES PATENTS

| | | |
|---|---|---|
| 3,197,466 | 7/1965 | Chow et al. ................ 260/239.1 |
| 3,219,669 | 11/1965 | Preud'homme et al. ...... 260/306.7 C |
| 3,288,800 | 11/1966 | Heuser et al. .............. 260/306.7 C |
| 3,544,581 | 12/1970 | Essery ....................... 260/239.1 |
| 3,586,667 | 6/1971 | Hatfield ..................... 260/239.1 |
| 3,741,959 | 6/1973 | Looker et al. .............. 260/239.1 |

OTHER PUBLICATIONS

Kirk–Othmer Encyclopedia of Chemical Technology, 2nd ed., pp. 660–661 (1967).

*Primary Examiner*—Gerald A. Schwartz
*Attorney, Agent, or Firm*—Lawrence S. Levinson; Merle J. Smith

[57] ABSTRACT

Compounds containing a cephem nucleus are prepared by heating a 1-oxide of a Schiff base of 6-aminopenicillanic acid. These cephem compounds are useful as intermediates in the preparation of physiologically active cephalosporins.

7 Claims, No Drawings

1-OXIDES OF SCHIFF BASES OF 6-AMINOPENICILLANIC ACID

PRIOR APPLICATIONS

This application is a division of our application Ser. No. 160,935, filed July 8, 1971, and now U.S. Pat. No. 3,862,181, granted Jan. 21, 1975; which in turn is a continuation-in-part of our application Ser. No. 84,946, filed Oct. 28, 1970, and now abandoned.

SUMMARY OF THE INVENTION

Prior to this invention, it was known that cephalosporins could be prepared from 1-oxides of penicillins (see U.S. Pat. No. 3,275,626). Although this process serves well if the desired cephalosporin end product contains the acyl group present in the penicillin reactant, it suffers the disadvantage of being specific in that it yields only a single cephalosporin product. Therefore, if a different cephalosporin is desired, the acyl group of the cephalosporin initially formed has to be removed and the product reacylated with the desired acylating reagent to give the correct cephalosporin product. Moreover, the process is limited to the use of penicillins which have acyl groups that are stable to the rearrangement conditions needed to form the cephalosporins. Therefore, to form a cephalosporin with an acyl group that is unstable, the acyl group of the cephalosporin formed from the stable penicillin has to be removed at the end of the reaction and replaced with the desired unstable acyl radical.

It has now been found that by utilizing a 1-oxide of a Schiff base (or imine) of 6-aminopenicillanic acid (6-APA) as the starting material, 7-amino-3-desacetoxycephalosporanic acid (7-ADCA) is obtained as the final product. This compound can then be acylated by any desired acylating agent to give the required cephalosporanic acid derivative. By this method the need to remove one acyl radical at the end of the process in order to form another acylated product is obviated and the attendant loss in yield and increase in cost are minimized.

More particularly, the present invention entails the heating of a 1-oxide of a Schiff base of 6-APA, with the carboxyl group protected (preferably in the form of an ester) in the presence of a catalyst, to yield the corresponding Schiff base of 7-ADCA derivative (which are new compounds of this invention), hydrolyzing the resulting Schiff base of 7-ADCA to remove the aldehyde, and, if desired, also hydrolyzing to remove the carboxylic acid protecting group to yield 7-ADCA as the final product. The order of this process may be reversed in which case a Schiff base of 7-ADCA is obtained, which may be hydrolyzed to 7-ADCA. The starting 1-oxides of Schiff bases of 6-APA are also new compounds of this invention which can be prepared by either treating a Schiff base of 6-APA with a suitable oxidizing (oxygenating) agent, or treating the 1-oxide of 6-APA (or a protected form thereof) with an aldehyde to yield the corresponding Schiff base.

DETAILED DESCRIPTION OF THE INVENTION

As stated above, in essence the process of this invention entails the heating of a 1-oxide of a Schiff base of 6-APA, in the form of a carboxyl group protected derivative thereof, to expand the penam ring to a cephem derivative. The 1-oxides (sulfoxides) occur in two isomeric forms, commonly designated as α or β. Most oxidations give rise to a mixture of isomers; either one or the mixture of isomers is suitable for this rearrangement process. Although any Schiff base of 6-APA, which is stable under the conditions of the reaction can be used, the preferred compounds, which are new intermediates of this invention, have the formula I:

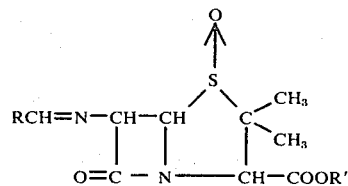

wherein R is any organic radical which does not interfere with the desired reaction and R' is an esterifying group.

Compounds of formula I are then heated to yield new cephem derivatives of this invention of the formula II:

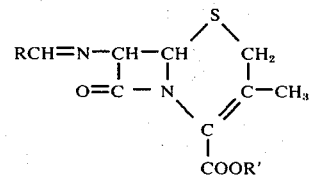

wherein R and R' are as hereinbefore defined.

To yield the known 7-ADCA products, compounds of formula II are then hydrolyzed to yield compounds of the formula III:

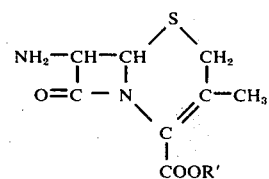

wherein R' is as hereinbefore defined. These compounds of formula III (either prior to or after removal of the R' group) can then be acylated with any desired acylating agent to yield the desired 3-desacetoxycephalosporin derivative or converted by any other method known in the art to any desired cephalosporin, containing acetoxymethyl, pyridinium methyl, or any other desired group in the 3-position.

One method for preparing compounds of formula I is by oxidizing a compound of the formula IV:

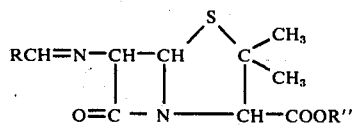

wherein R is as hereinbefore defined and R'' is hydrogen, a cation or an esterifying group. The oxidation is accomplished by treating the Schiff base of formula IV with an equivalent amount of an oxidizing or oxygenating agent, such as an organic peracid (e.g., m-chloroperbenzoic acid, peracetic acid and performic acid), hydrogen peroxide, ozone, an alkali metal periodate (e.g., sodium periodate) or iodosobenzene. The reaction is preferably conduccted in an inert organic solvent for the Schiff base reactant, such as methylene chloride, benzene, dimethoxyethane, dioxane, isobutyl alcohol, methanol, isopropanol, isopropanol, ethyl acetate, or chloroform. With some stable Schiff bases (e.g., from salicylaldehyde) water may be used as a cosolvent if desired. The reaction is preferably carried out at a temperature in the range of about −10° to about 30° C.

Suitable compounds of formula IV include any Schiff base of 6-APA (or a protected form thereof). When using this process, the preferred Schiff bases are those formed with aldehydes which do not interfere or compete in the oxidation reaction. Thus, although any of the Schiff bases of 6-APA disclosed in U.S. Pat. No. 3,288,800 can be used, the preferred compounds are those formed with carbocyclic aromatic aldehydes, such as those of the formula: RCHO, wherein R is phenyl, hydroxy phenyl (e.g., o-hydroxyphenyl), naphthyl, nitrophenyl (e.g., m-nitrophenyl), halophenyl (e.g., p-chlorophenyl, m-fluorophenyl and o-bromophenyl), halohydroxyphenyl (e.g., p-chloro-o-hydroxyphenyl), carbo(lower alkoxy)phenyl (e.g., p-carbomethoxyphenyl, o-carboethoxyphenyl, p-carbohexyloxyphenyl, and m-carbobutoxyphenyl), lower alkoxyphenyl (e.g., o-methoxyphenyl, p-methoxyphenyl, m-methoxyphenyl, p-ethoxyphenyl, o-n-propoxyphenyl, and p-n-hexyloxyphenyl), di(lower alkyl)aminophenyl [e.g., p-dimethylaminophenyl, o-diethylaminophenyl, p-(N-n-butyl-N-methylamino)phenyl, and m-di-n-pentylaminophenyl], and the correspondingly substituted naphthaldehyde derivatives, such as o-hydroxynaphthaldehyde. In addition to the aldehydes mentioned above, other suitable aldehydes include alkanals (e.g., acetaldehyde, n-butanal, isopentaldehyde, pivaloaldehyde, heptaldehyde, octaldehyde, 2-ethylhexaldehyde, nonylaldehyde, capraldehyde and lauraldehyde); substituted alkanals, such as halo, hydroxy, nitro and alkoxy substituted alkanals; carbocyclic aralkanals wherein the alkanol group contains two or more carbon atoms (e.g., phenacetaldehyde, hydrocinnamaldehyde and 2-phenylpropionaldehyde); carbocyclic aralkenals (e.g., phenyl(lower alkenals) such as cinnamaldehyde); and heterocyclic substituted alkanals (e.g., 2-furaldehyde, 2-thiophenealdehyde and pyridine-4-aldehyde).

Compounds of the formula IV can be used in either their free acid form, their salt form, or in the form of an ester. Suitable salt forms include those with alkali metals (e.g., sodium and potassium), alkaline earth metals (e.g., calcium), ammonium and amines, such as alkylamines (e.g., methylamine, ethylamine, tert.-ocylamine, dodecylamine and tetradecylamine), aralkylamines (e.g., benzylamine and phenethylamine), dialkylamines (e.g., dimethylamine and diethylamine), trialkylamines (e.g., triethylamine), diaralkylamines (e.g., dibenzylamine), lower alkylene diamines and N-substituted derivatives thereof (e.g., ethylenediamine and N,N-dibenzylethylenediamine), heterocyclic amines (e.g., pyridine and N-methylmorpholine) and any other amine which will not interfere with the oxidation reaction. Suitable esters include those formed with lower alkanols (e.g., methanol, ethanol and tert.-butanol), cycloalkanols (e.g., cyclohexanol and cyclopentanol), carbocyclic aryl alcohols (e.g., phenol and 2-naphthol), carbocyclic ar(lower alkanols), (e.g., benzyl alcohol, benzhydrol, 1-naphthylmethyl alcohol and 2-phenylethanol), trimethylsilyl, lower alkanoyl(lower alkanols) (e.g., hydroxyacetone and pivaloylmethanol), carbocyclic aroyl(lower alkanols) (e.g., benzoylmethanol, 2-benzoylethanol and 2-naphthylcarbonylmethanol), cycloalkylcarbonyl(lower alkanols) (e.g., hydroxymethylcyclohexylketone), lower alkanoyloxy (lower alkanols) (e.g., pivaloyloxymethanol), carbocyclic aroyloxy (lower alkanols) (e.g., benzoyloxymethanol) and substituted derivatives of any of the above, such as lower alkyl (e.g., methyl and ethyl), lower alkoxy (e.g., methoxy and butoxy), halo (e.g., chloro, fluoro and bromo), and nitro derivatives, as exemplified by 2,2,2-trichloroethanol, 2-bromoethanol, p-nitrophenol, p-methoxyphenol, p-methoxybenzyl alcohol, p-nitrobenzyl alcohol p,p'-dimethoxybenzhydrol, 2-dimethylaminoethanol, p-nitrobenzoylmethanol and p-methoxybenzoylmethanol. If the compound of formula IV is initially in its free acid or salt form it can be converted to its ester form by reaction with a suitable alcohol, in the presence of an ester forming reagent, such as phosgene and dicyclohexylcarbodiimide; or with an alkyl or aralkyl halide (e.g., benzyl chloride); or by conversion to an active form (e.g., mixed anhydride or p-nitrophenyl ester) followed by reaction with an alcohol; or by reaction of the free acid with diazoalkanes or aralkanes, such as diazomethane and phenyldiazomethane; or any other method well known in the art for forming esters.

Alternatively, compounds of formula I can be prepared by interacting a 1-oxide or 6-APA or a protected form thereof of the formula V:

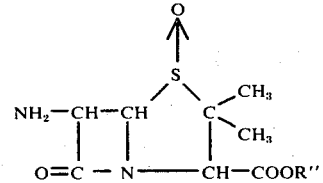

wherein R'' is as hereinbefore defined, with an aldehyde of the formula: RCHO, wherein R is as hereinbefore defined, in the manner well known in the art, to yield a compound of formula I (or the free acid or salt form thereof, which then can be converted to the ester by one of the methods stated above). Suitable compounds of the formula V include the 1-oxide of 6-APA and those salts and esters that correspond to the specific salts and esters of the compounds of formula IV, specifically mentioned hereinbefore. Suitable aldehydes include aldehydes formed from any of the R groups specifically mentioned hereinbefore. This latter process is the preferred one for forming compounds of formula I which are Schiff bases with aldehydes that contain groups which could interfere or enter into an oxygenation reaction thereby decreasing the yield of the desired 1-oxide if used in starting materials in the first process.

Compounds of the formula II are then formed by heating a compound of the formula I in the presence of a catalyst, the compound of the formula I preferably being dissolved in an inert organic solvent. Suitable catalysts include acidic agents, e.g., inorganic acids, such as sulfuric acid, organic acids, such as sulfonic acids as exemplified by the lower alkane sulfonic acids (e.g., methane and ethane sulfonic acid), and carbocyclic aryl sulfonic acids (e.g., p-toluenesulfonic acid and 1-naphthalenesulfonic acid); and carboxylic acids, as exemplified by the halo substituted lower alkanoic acids (e.g., trifluoroacetic acid), and carbocyclic aromatic acids (e.g., benzoic and phthalic acid); the corresponding anhydrides of any of the above (e.g., trifluoroacetic anhydride, acetic anhydride, benzoic anhydride, and phthalic anhydride); stannic chloride and aluminum chloride. Amine salt catalysts include the pyridine salts of methane sulfonic acid, p-toluenesulfonic acid, dichloromethanephosphoric acid, naphthalene-2-sulfonic acid, and trifluoroacetic acid, as examples. In general, various phosphoric and sulfonic acid salts of nitrogen bases of pKb greater than 4, preferably greater than 7, may be employed. Various primary, secondary and tertiary mono- or polyfunctional nitrogen bases may be used, including quinoline, benzimidazole and substituted analogs; aniline, and dimethylaniline.

Suitable solvents include toluene, dimethylformamide, diglyme, xylene, dimethylacetamide, benzene, ethylene dichloride and tetramethylurea. The rearrangement reaction is preferably carried out at a temperature in the range of about 70° C. to about 145° C.

Compounds of the formula II are then converted to compounds of the formula III by hydrolysis in the presence of a mild aqueous acid, such as hydrochloric, sulfuric, formic, oxalic, β-toluenesulfonic, trifluoroacetic and acetic acid. To improve the cleavage an acceptor amine, such as aniline, may be present in the reaction mixture.

The compound of formula II which contains an ester group may be converted to its free carboxylic acid or salt by hydrolyzing the compound of formula II either before, during or after the removal of the Schiff base. The method of hydrolysis depends on the nature of the protecting group and its ease of removal. Therefore, when a free acid or salt is desired as the final product, the ester group is chosen so that it can be readily removed. For example, if a trimethyl silyl ester is used, it can be removed by mild aqueous or alcoholic acid, such as dilute hydrochloric or acetic acid; if a trichloroethyl ester is used, it can be removed by treatment with zinc in acetic acid or dimethylformamide; if a p-methoxybenzyl ester is used, it can be removed by treatment with mild acid, such as anhydrous trifluoroacetic acid, hydrogen bromide in acetic acid or sulfuric acid in anisole/benzene.

The compounds of the formula III, thus formed, can be acylated in the manner well known in the art to yield 3-desacetoxycephalosporins of known pharmaceutical activity.

The following examples illustrate the invention (all temperatures being in centigrade):

EXAMPLE 1

N-Benzylidene-6-aminopenicillanic Acid, Methyl Ester Sulfoxide (a) Preparation of N-Benzylidene-6-aminopenicillanic Acid:

73.8 mmoles of N-benzylidene-6-aminopenicillanic acid, tertiary octylamine salt are added to 240 ml. of methylene chloride cooled to 0°–5° (ice-water bath). After dispersion, 158.4 mmoles of benzaldehyde are added. This is followed by the addition over 30 minutes of an 8 ml. tetrahydrofuran solution containing 76.2 mmoles of trifluoroacetic acid. During the course of this addition the reaction mixture gradually clarifies to finally form a clear, slightly yellow solution. The reaction mixture is then allowed to reach room temperature over a period of 1 hour before being concentrated to one-third volume in vacuo at a temperature not exceeding 30°. On cooling of the concentrate in a refrigerator, the desired product crystallizes out in a yield of about 82 mole percent.

(b) Preparation of N-Benzylidene-6-aminopenicillanic Acid, Methyl Ester:

35 mmoles of N-benzylidene-6-aminopenicillanic acid are dissolved in 25 ml. of glyme and excess diazomethane in ether is added. The mixture is allowed to stand for 15 minutes before being evaporated to one-third its volume. On cooling the ester crystallizes out in about 82% yield.

(c) Preparation of N-Benzylidene-6-aminopenicillanic Acid, Methyl Ester, Sulfoxide:

3.2 mmoles of N-benzylidene-6-aminopenicillanic acid, methyl ester are dissolved in 50 ml. of dry dioxane and 3.2 mmoles of m-chloroperbenzoic acid dissolved in 20 ml. of dioxane are added dropwise. The reaction is allowed to proceed at room temperature until no more peracid can be detected. The reaction mixture is then diluted with chloroform and washed with an aqueous solution at pH 7.2. The organic layer is dried and evaporated to give a brown oil. On purification this gives the desired product in about 20% yield.

EXAMPLE 2

N-Salicylidene-6-aminopenicillanic Acid, Methyl Ester Sulfoxide (a) Preparation of N-Salicylidene-6-aminopenicillanic Acid:

25.2 mmoles of N-salicylidene-6-aminopenicillanic acid, tertiary-octylamine salt are added to 100 ml. of methylene chloride and cooled to 5°. After dispersion, 50 mmoles of salicylaldehyde are added, followed by the addition of 25.7 mmoles of trifluoroacetic acid. The product crystallizes out during reaction in about 78% yield.

(b) Preparation of N-Salicylidene-6-aminopenicillanic Acid, Methyl Ester:

25 mmoles of N-salicylidene-6-aminopenicillanic acid are dissolved in 25 ml. of methanol and an excess of ethereal diazomethane solution is added. The mixture is allowed to stand for 15 minutes before being evaporated to dryness to give a yellow oil. This is washed with dilute cold base to give the ester in about 92% yield.

(c) Preparation of N-Salicylidene-6-aminopenicillanic Acid, Methyl Ester, Sulfoxide:

27.2 mmoles of N-salicylidene-6-aminopenicillanic acid, methyl ester are dissolved in 360 ml. of dry dichloromethane. Then 27.2 mmoles of m-chloroperbenzoic acid dissolved in 40 ml. of dry dichloromethane are added slowly. The reaction is allowed to proceed for 45 minutes before being diluted with dichloromethane and being washed with an aqueous solution at pH 7.2. The organic extract is dried and evaporated to give the desired sulfoxide in about 78% yield; after one recrystallization, m.p. about 146°–149°.

EXAMPLE 3

N-Salicylidene-6-aminopenicillanic Acid, Trichloroethyl Ester, Sulfoxide (a) Preparation of N-Salicylidene-6-aminopenicillanic Acid, Trichloroethyl Ester:

29.9 mmoles of N-salicylidene-6-aminopenicillanic acid are dissolved in 150 ml. of dichloromethane and 165 mmoles of 2,2,2-trichloroethanol are added followed by the addition of 29.9 mmoles of dicyclohexylcarbodiimide. The latter dissolves quickly and is followed by the precipitation of dicyclohexylurea. After stirring for 90 minutes, the urea is filtered off and washed with dichloromethane. The filtrate is diluted with dichloromethane and washed with cold water at pH 3.5 and again at pH 7.2. The organic layer is then evaporated to dryness and digested with benzene. After removal of the solids, the benzene is evaporated in vacuo. The resulting oil is crystallized from chloroform-ether to give the desired product in about 69% yield, m.p. about 145°–150°.

(b) Preparation of N-Salicylidene-6-aminopenicillanic Acid, Trichloroethyl Ester, Sulfoxide:

Following the procedure of Example 2(c) but substituting an equivalent amount of N-salicylidene-6-aminopenicillanic acid, trichloroethyl ester for the methyl ester, N-salicylidene-6-aminopenicillanic acid, trichloroethyl ester, sulfoxide, is obtained in a yield of about 77%, m.p. about 138°–155°.

EXAMPLE 4

N-Salicylidene-6-aminopenicillanic Acid, Sulfoxide 312 mmoles (1.00 g) of N-salicylidene-6-aminopenicillanic acid are dissolved in 300 ml. of methylene chloride. To this is added 312 mmoles of m-chloroperbenzoic acid in 100 ml. of methylene chloride over 20 minutes at room temperature. The reaction is complete in 30 minutes. The mixture is concentrated and triturated with ether. The yield is about 90%.

EXAMPLE 5

N-Salicylidene-6-aminopenicillanic Acid, 2,2,2-Trichloroethyl Ester, Sulfoxide 22.5 mmoles of N-salicylidene-6-aminopenicillanic acid, sulfoxide, are dissolved in dichloromethane and 112.5 mmoles of pyridine. To the well stirred solution are added 112.5 mmoles of trichloroethanol and 22.5 mmoles of dicyclohexylcarbodiimide. After 90 minutes the precipitated dicyclohexylurea is filtered off and washed with mild acid and base, dried, and evaporated in vacuo. Digestion with benzene and evaporation of the filtrate gives the desired product in about 75% yield.

EXAMPLE 6

N-Salicylidene-6-aminopenicillanic Acid, Methyl Ester, Sulfoxide (a) Preparation of 6-Aminopenicillanic Acid Sulfoxide:

9.26 mmoles of 6-aminopenicillanic acid is slurried in 100 ml. of water. To this is added 9.26 ml. of 1N hydrochloric acid at 5°. Over a 20 minute period, 9.2 mmoles of m-chloroperbenzoic acid in 100 ml. of dioxane are added. The reaction is stirred at 5° for 2 hours at which time thin layer chromatography on silica gel shows all the starting material is gone and one product has appeared. The dioxane is removed under reduced pressure and the m-chlorobenzoic acid is extracted with ether. The product is freeze-dried to remove the water.

(b) Preparation of 6-Aminopenicillanic Acid, Methyl Ester Sulfoxide:

4 mmoles of 6-aminopenicillanic acid sulfoxide is dissolved in 75 ml. of methanol. To this is added 12 mmoles of diazomethane in 40 ml. of ether at 5°. This is stirred for ½ hour and the solvents removed under reduced pressure to give the desired product.

(c) Preparation of N-Salicylidene-6-aminopenicillanic Acid, Methyl Ester Sulfoxide:

A suspension of 0.1 ml. of methyl 6-aminopenicillanate, sulfoxide, in 200 ml. of chloroform is treated with 0.11 mole of salicylaldehyde and 0.1 ml. of triethylamine is added. After stirring at room temperature for 4 hours, the mixture is washed with cold 1% aqueous sodium bicarbonate and cold water. After drying over sodium sulfate for about one hour, the solution is evaporated to dryness to deposit the product, which forms a powder on trituration with ether.

EXAMPLE 7

N-Salicylidene-6-aminopenicillanic Acid Sulfoxide 9.26 mmoles of 6-aminopenicillanic acid is dissolved in 100 ml. of water and cooled to 50°. To this is added 9.26 ml. of 1N hydrochloric acid. Then 9.20 mmole of m-chloroperbenzoic acid in 100 ml. of dioxane is added over 20 minutes. This is stirred for 2 hours at 5°. None of the starting material remains and 6-aminopenicillanic acid sulfoxide has formed as evidenced by thin layer chromatography. The solvents are concentrated and the m-chlorobenzoic acid extracted with ether. The solution of 6-aminopenicillanic acid sulfoxide is stirred with 9.3 mmoles of salicylaldehyde for 30 minutes and then evaporated to dryness at reduced pressure. The residue is triturated with chloroform and filtered. Evaporation of the chloroform and trituration with ether deposits the product.

EXAMPLE 8

N-Salicylidene-6-aminopenicillanic Acid, Benzyl Ester, Sulfoxide

By substituting 0.112 mole of benzyl alcohol for the 2,2,2-trichloroethanol in Example 5, the desired product is obtained.

EXAMPLE 9

N-Salicylidene-6-aminopenicillanic Acid, p-Methoxybenzyl Ester, Sulfoxide

By substituting 0.112 mole of p-methoxybenzyl alcohol for the 2,2,2-trichloroethanol in Example 5, the desired product is obtained.

EXAMPLE 10

N-Salicylidene-6-aminopenicillanic Acid, Pivaloyloxymethyl Ester, Sulfoxide

By substituting 0.112 mole of pivaloyloxymethanol for the 2,2,2-trichloroethanol in Example 5, the desired product is obtained.

EXAMPLE 11

N-Pivalylidene-6-aminopenicillanic Acid, Methyl Ester, Sulfoxide

A solution of 1 equivalent of pivaloaldehyde and 1 equivalent of the methyl ester of 6-aminopenicillanic acid sulfoxide in benzene is treated with excess drying agent (Linde 4A Molecular Sieves) overnight at room temperature. Evaporation at reduced pressure leaves the product as an oil.

Similarly, by following the procedure of Examples 6 and 7 and substituting an equivalent amount of the indicated aldehyde for the salicyaldehyde in these Examples, the indicated Schiff base of 6-aminopenicillanic acid sulfoxide, in either its methyl ester or free acid form, respectively, is formed:

| Example | Aldehyde | Schiff Base Product |
|---|---|---|
| 12 | 1-Naphthylaldehyde | 1-Naphthylidene |
| 13 | m-Nitrobenzaldehyde | m-Nitrobenzylidene |
| 14 | p-Chlorobenzaldehyde | p-Chlorobenzylidene |
| 15 | p-Carbomethoxybenzaldehyde | p-Carbomethoxybenzylidene |
| 16 | p-Ethoxybenzaldehyde | p-Ethoxybenzylidene |
| 17 | o-Diethylaminobenzaldehyde | o-Diethylaminobenzylidene |
| 18 | n-Octaldehyde | n-Octylidene |
| 19 | Phenylacetaldehyde | Phenylethylidene |
| 20 | 2-Furaldehyde | 2-Furylmethylidene |

EXAMPLE 21

Benzoyloxymethyl N-Benzylidene-6-aminopenicillanate Sulfoxide (a) Preparation of Benzoyloxymethyl N-Benzylidene-6-aminopenicillanate:

To a solution of 100 mmoles of N-benzylidene-6-aminopenicillanic acid in 250 ml. of methylene chloride there is added 100 mmoles of triethylamine, followed by the dropwise addition of 100 mmoles of benzoyloxymethyl chloride in 50 ml. of methylene chloride. The reaction mixture is stirred vigorously during the addition, while the temperature is maintained at 20°–25°. The reaction mixture is then diluted with anhydrous ether to precipitate the triethylamine hydrochloride and the filtrate concentrated under reduced pressure to yield the desired product.

(b) Preparation of Benzoyloxymethyl N-Benzylidene-6-aminopenicillanate, Sulfoxide:

Following the procedure of Example 1c, but substituting an equivalent amount of benzoyloxymethyl N-benzylidene-6-aminopenicillanate for the N-benzylidene-6-aminopenicillanic acid, methyl ester, there is obtained the desired product.

EXAMPLE 22

N-Salicylidene-6-Aminopenicillanic Acid, p-Methoxybenzyl Ester, Sulfoxide (a) Preparation of N-salicylidene-6-aminopenicillanic acid:

300 g. of N-salicylidene-6-aminopenicillanic acid, tert.-n-octylamine salt is slurried in 1200 ml. of methylenedichloride. A solution of 51.6 ml. of trifluoroacetic acid in 135 ml. of methylenedichloride is added over a 15-minute period. The salt dissolves and in a few minutes the free acid crystallizes in large rectangular prisms. The mixture is cooled and agitated for two hours. After filtration the crystals are washed twice with 160 ml. of methylenedichloride. Yield about 209.4 g. (theory 212 g.)

(b) Preparation of N-salicylidene-6-aminopenicillanic acid, sulfoxide:

11.4 g. of N-salicylidene-6-aminopenicillanic acid (estimated to contain 10 g. of pure acid) is dissolved in 100 ml. of isobutyl acetate and a solution of 6.3 g. of m-chloroperbenzoic acid (85% purity) in 20 ml. of isobutyl acetate is added over a period of one-half hour. After one hour agitation at room temperature (negative Starch-Iodide test) the fine needles are filtered and washed with 10 ml. of isobutyl acetate to yield about 7.66 g. of product. Recrystallization from methanol gives a product with the following analysis:

Anal. for $C_{15}H_{16}N_2O_5S$ (M 336.37). Calc.: C, 53.55; H, 4.79; N, 8.33; S, 9.53, Found: C, 53.66; H, 4.72; N, 8.37; S, 9.69.

(c) Preparation of the p-methoxybenzyl ester of N-salicylidene-6-aminopenicillanic acid, sulfoxide:

16.8 g. of N-salicylidene-6-aminopenicillanic acid, sulfoxide is slurried in 200 ml. of methylenedichloride (dried with Molecular Sieves) and cooled to 3°–5°. 8.15 ml. of pyridine (100 mm.) is added followed by 12.5 ml. of p-methoxybenzyl alcohol (100 mm.). A clear solution results. A solution of 12.5 g. of dicyclohexylcarbodiimide (60 mm.) in 50 ml. of dried methylenedichloride is then added dropwise over a period of ½ hour, while maintaining a temperature of 3°–5°. Five minutes after start of the addition, dicyclohexylurea starts to precipitate indicating a reaction. The reaction is continued for ½ hour in the cold and completed by ½ hour at room temperature and 1 hour at 35°–40°. After holding the mixture in the cold for 1 hour, the dicyclohexylurea by-product is filtered off. The filtrate is then washed twice with 200 ml. of water, once at pH 3.5 and then at pH 7.5. After separation, the methylenedichloride solution is dried with 20 g. of anhydrous magnesium sulfate, filtered, and washed with 35 ml. of dried methylenedichloride. The filtrate is concentrated under vacuum to about 75 ml., clarified, and mixed with 100 ml. of isopropyl alcohol. The residual methylenedichloride is removed by further concentration and the product is allowed to crystallize for 1 hour at room temperature and 1 hour in the cold. Filtration followed by washes of 25 ml. of isopropyl alcohol and 40 ml. of ether gives on drying about 17.6 g. of product. Yield about 77%. M.P. about 127°–129°.

Anal. for $C_{23}H_{24}N_2O_6S$ (M 456.52): Calc.: C, 60.51 H, 5.30; N, 6.14; S, 7.02 Found: C, 60.68; H, 5.31; N, 6.06; S, 7.04

EXAMPLE 23

N-Salicylidene-7-amino-3-desacetoxycephalosporanic Acid, Methyl Ester 2.5 mmoles of N-salicylidene-6-aminopenicillanic acid, methyl ester, sulfoxide, are suspended in 15 ml. of toluene and a catalytic amount of p-toluenesulfonic acid is added. The reaction mixture is then refluxed for 1 hour. After cooling, the solution is diluted with chloroform and washed with an aqueous solution at pH 7.2. The organic extracts are dried and evaporated to give an oil. This is purified by preparative thin layer chromatography on silica gel to give the desired rearranged product, m.p. about 167°–169°.

EXAMPLE 24

N-Salicylidene-7-amino-3-desacetoxycephalosporanic Acid, Trichloroethyl Ester 1.5 mmoles of N-salicylidene-6-aminopenicillanic acid, 2,2,2-trichloroethyl ester, sulfoxide are dissolved in 50 ml. of dimethylformamide and 1 ml. of acetic anhydride is added. The reaction vessel is then immersed in an oil bath at 125° for 1 hour. The dimethylformamide is then evaporated in vacuo to leave a brown oil. The desired rearranged product is separated by preparative thin layer chromatography on silica gel.

EXAMPLE 25

N-Salicylidene-7-amino-3-desacetoxycephalosporanic Acid, Methyl Ester 0.29 mmoles of N-salicylidene-6-aminopenicillanic acid, methyl ester, sulfoxide are dissolved in 10 ml. of dimethylformamide and 0.12 ml. of acetic anhydride are added. The reaction vessel is then submerged in an oil bath at 125° for 1 hour. The dimethylformamide is then evaporated in vacuo to leave a brown oil. The desired rearranged product is separated by preparative thin layer chromatography on silica gel.

EXAMPLE 26

N-Benzylidene-7-amino-3-desacetoxycephalosporanic Acid, Methyl Ester

Following the procedure in Example 23 but using an equivalent amount of N-benzylidene-6-aminopenicillanic acid, methyl ester, sulfoxide for the N-salicylidene compound, N-benzylidene-7-amino-3-desacetoxycephalosporanic acid, methyl ester, is obtained.

EXAMPLE 27

N-Salicylidene-7-amino-3-desacetoxycephalosporanic Acid, p-Methoxybenzyl Ester

Following the procedure of Example 23 but substituting 2.5 mmoles of N-salicylidene-6-aminopenicillanic acid, p-methoxybenzyl ester, sulfoxide, for the sulfoxide used in the Example, the desired product is obtained.

EXAMPLE 28

N-Salicylidene-7-amino-3-desacetoxycephalosporanic Acid, 2,2,2-Trichloroethyl Ester Following the procedure of Example 23 but substituting 2.5 mmoles of N-salicylidene-6-aminopenicillanic acid, 2,2,2-trichloroethyl ester, sulfoxide, for the sulfoxide used in the Example, the desired product is obtained.

EXAMPLE 29

Benzoyloxymethyl N-Benzylidene-7-amino-3-desacetoxycephalosporanate

Following the procedure of Example 23 but substituting an equivalent amount of benzoyloxymethyl N-benzylidene-6-aminopenicillanate, sulfoxide for the N-salicylidene-6-aminopenicillanic acid, methyl ester sulfoxide, there is obtained the desired product.

Similarly, by following the procedure of Example 23 but substituting 2.5 mmoles of the indicated N-X-6-aminopenicillanic acid, methyl ester, sulfoxide for the N-salicylidene-6-aminopenicillanic acid, methyl ester sulfoxide, the designated N-X-7-amino-3-desacetoxycephalosporanic acid methyl ester is formed.

| Example | Reactant (X is) | Product (X is) |
|---|---|---|
| 30 | Pivalylidene | Pivalylidene |
| 31 | 1-Naphthylidene | 1-Naphthylidene |
| 32 | m-Nitrobenzylidene | m-Nitrobenzylidene |
| 33 | p-Chlorobenzylidene | p-Chlorobenzylidene |
| 34 | p-Carbomethoxy-benzylidene | p-Carbomethoxy-benzylidene |
| 35 | p-Ethoxybenzylidene | p-Ethoxybenzylidene |
| 36 | o-Diethylamino-benzylidene | o-Diethylamino-benzylidene |
| 37 | n-Octylidene | n-Octylidene |
| 38 | Phenylethylidene | Phenylethylidene |
| 39 | 2-Furylmethylidene | 2-Furylmethylidene |

EXAMPLE 40

N-Salicylidene-7-amino-3-desacetoxycephalosporanic Acid, p-Methoxybenzyl Ester 500 mg. of the p-methoxybenzyl ester of N-salicylidene-6-aminopenicillanic acid, sulfoxide is dissolved in 75 ml. of benzene followed by the addition of 100 mg. of (dichloromethyl) phosphoric acid pyridine salt, 0.1 ml. of salicylaldehyde and 0.1 ml. of pyridine. The mixture is heated under gentle reflux for 19 hours, drying the condensate with molecular sievers (Linde 4A). After cooling to room temperature, the solution is clarified and concentrated to dryness. After slurrying in warm 95% ethanol and cooling to room temperature, the crystals are filtered and washed with 95% ethanol. Yield about 220 mg. (46%) of product, melting point about 167°. From the mother liquor an additional 10 mg. of product can be obtained by adding hexane. Concentration of the second mother liquor to dryness gives material (about 300 mg.) containing about 60 mg. of product.

EXAMPLE 41

N-Salicylidene-7-amino-3-desacetoxycephalosporanic Acid 100 mg. of N-salicylidene-7-amino-3-desactoxycephalosporanic acid, 2,2,2-trichloroethyl ester is dissolved in 2 ml. of 90% acetic acid at 0°. Then 400 mg. of zinc dust are added and the reaction is allowed to proceed for one hour. The zinc is then removed by filtration and the acetic acid evaporated to leave the desired product as a solid.

EXAMPLE 42

N-Salicylidene-7-amino-3-desacetoxycephalosporanic Acid

One gram of N-salicylidene-7-amino-3-desacetoxycephalosporanic acid p-methoxybenzyl ester is treated with 30 ml. of trifluoroacetic acid at 0° for 15 minutes. The solution is evaporated at reduced pressure and triturated with ether to give the product as a powder. m. p. about 197°–198°.

In a manner similar to that of Examples 41 and 42 all other esters of Schiff bases of 7-ADCA can be converted to their free acid. Treatment of the acid with a desired base yields the corresponding salt.

EXAMPLE 43

7-Amino-3-desacetoxycephalosporanic Acid, Methyl Ester

A solution of N-salicylidene-7-amino-3-desacetoxycephalosporanic acid methyl ester in dimethoxyethane/water (2:1) is treated with one equivalent of 1N hydrochloric acid and an equivalent of aniline for two hours. The solution is then diluted with water and extracted with ether. The aqueous layer is adjusted to pH 7.5 and extracted with ethyl acetate. The organic layer is dried (sodium sulfate) and evaporated at reduced pressure at room temperature to deposit the desired product.

EXAMPLE 44

7-Amino-3-desacetoxycephalosporanic Acid, 2,2,2-Trichloroethyl Ester

A mixture of 10 mmoles of N-salicylidene-7-amino-3-desacetoxycephalosporanic acid, 2,2,2-trichloroethyl ester in 100 ml. of 0.1N hydrochloric acid and 50 ml. of ether is stirred rapidly for 45 minutes. The aqueous solution is separated, made basic (pH 7.5 to 8) and extracted with ethyl acetate. The ethyl acetate layer is dried (sodium sulfate) and evaporated to isolate the desired product.

EXAMPLE 45

7-Amino-3-desacetoxycephalosporanic Acid 1-mmole of N-salicylidene-7-amino-3-desacetoxycephalosporanic acid in 10 ml. of 1:1 dioxane/water is treated with 1 mmole of aniline and 1 ml. of 1N hydrochloric acid. After stirring at room temperature for one hour the pH is adjusted to 4.5. The organic layer is separated and the aqueous suspension is concentrated to about ½ its volume to complete the precipitation of the 7-ADCA product.

EXAMPLE 46

7-Amino-3-desacetoxycephalosporanic Acid 1 mmole of N-benzylidene-7-amino-3-desacetoxycephalosporanic acid in 10 ml. of 1:1 dioxane/water is treated with one ml. of 1N hydrochloric acid. After stirring at room temperature for 1 hour the pH is adjusted to 4.5. The organic layer is separated and the aqueous suspension is concentrated to about ½ its volume to complete the precipitation of the 7-ADCA product.

EXAMPLE 47

7-Amino-3-desacetoxycephalosporanic Acid

A mixture of 10 mmoles of benzyloxycarbonyl N-benzylidene-7-amino-3-acetoxycephalosporanate in 100 ml. of 1:1 dioxane/water is treated with 10 ml. of 1 N hydrochloric acid. The mixture is stirred for 1 hour at room temperature and extracted several times with ether. To the aqueous solution is added 100 mg. of 5% palladium-on-carbon and the mixture is shaken in an atmosphere of hydrogen at 20 lbs. pressure until the absorption of hydrogen is completed. The reaction mixture is filtered and the pH adjusted to 4.5 by the addition of dilute aqueous sodium hydroxide. The filtrate is then concentrated to about ⅓ its volume to complete the precipitation of the 7-amino-3-desacetoxycephalosporanic acid.

Similarly, by following the procedures of Examples 44 through 48, all other Schiff's bases of 7-ADCA or esters thereof can be converted to 7-ADCA or an ester derivative.

In the foregoing examples, the process has been shown stepwise with the isolation of each intermediate. In actual practice this need not be done and in fact it may be preferable to carry out more than one step of the process in the same reaction vessel without isolating the intermediate formed. This is more clearly shown in the following examples:

EXAMPLE 48

N-Salicylidene-7-amino-3-desacetoxycephalosporanic acid 30 mmoles of N-salicylidene-6-aminopenicillanic acid are dissolved in 150 ml. of dichloromethane and 165 mmoles of trichloroethanol are added followed by the addition of 30 mmoles of dicyclohexylcarbodiimide. After stirring for 90 minutes at room temperature, the precipitated dicyclohexylurea is removed by filtration. Then 30 mmoles of m-chloroperbenzoic acid dissolved in 50 ml. of dichloromethane are added slowly to the stirred filtrate. The reaction is allowed to proceed for 45 minutes before being diluted with dichloromethane and washed with an aqueous solution at pH 7.2. After evaporation of the solvent, the resulting oil is dissolved in 50 ml. of dimethylformamide. 25 ml. of acetic anhydride are added and the reaction vessel is immersed in an oil bath at 130° for 1 hour. The dimethylformamide solution is then cooled and concentrated to 10 ml. in vacuo. Then 15 ml. of glacial acetic acid are added followed by the addition of 40 g. of zinc dust. The reaction is stirred for 1 hour at room temperature. All the solvents are then removed in vacuo to leave a solid. This is suspended in chloroform and washed with dilute cold sodium bicarbonate. The basic layer is acidified and extracted to give N-salicylidene-7-amino-3-desacetoxycephalosporanic acid.

EXAMPLE 49

7-Amino-3-desacetoxycephalosporanic Acid 5.5 g. of N-salicylidene-7-amino-3-desacetoxycephalosporanic acid, p-methoxybenzyl ester, is mixed with 25 ml. of anisole and cooled to 3° C. 25 ml. of cold trifluoroacetic acid is added and the solution is agitated 2 and ½ hours at room temperature. The solution is then cooled to 1°–3° C. and 50 ml. of n-butanol is added. 45 ml. of triethylamine is added dropwise while maintaining cooling over a period of ½ hour to neutralize the acid. The Schiff base is then hydrolyzed by adding 50 ml. of water and 2 ml. of aniline and agitating for one hour at room temperature. The crystalline material is filtered off and washed with n-butanol and acetone. Drying yields about 2.45 g. of 7-amino-3-desacetoxycephalosporanic acid.

What is claimed is:
1. A compound of the formula

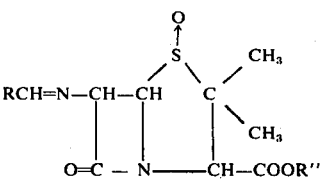

wherein R is a monocyclic or dicyclic carbocyclic aromatic group; alkyl; halo, hydroxy, nitro or alkoxy substituted alkyl; monocyclic carbocyclic aryl(lower alkyl); monocyclic carbocyclic aryl(lower alkenyl); furyl; thiophenyl; or pyridyl and R'' is hydrogen; an alkali metal, alkaline earth metal, ammonium or organic ammonium radical; or a conventional esterifying group.

2. The compound of claim 1 wherein R is a monocyclic carbocyclic aromatic group and R'' is a conventional esterifying group.

3. The compound of claim 1 wherein R is phenyl and R'' is a conventional esterifying group.

4. The compound of claim 1 wherein R is o-hydroxyphenyl and R'' is a conventional esterifying group.

5. The compound of claim 4 wherein R'' is p-methoxybenzyl.

6. The compound of claim 1 wherein R is phenyl, naphthyl, alkyl, phenyl(lower alkyl) or phenyl(lower alkenyl); halo, hydroxy, nitro or alkoxy substituted derivatives of any of the foregoing; furyl; thiophenyl; or pyridyl.

7. The compound of claim 6 wherein R'' is lower alkyl, cycloalkyl, phenyl, napthyl, phenyl(lower alkyl), naphthyl(lower alkyl), benzhydryl, trimethylsilyl, lower alkanoyl(lower alkyl), benzoyl(lower alkyl), naphthylcarbonyl(lower alkyl), cyanoalkylcarbonyl, or lower alkanoyl(lower alkyl); or lower alkyl, lower alkoxy, halo or nitro substituted derivatives of any of the foregoing.

* * * * *